US00PP22331P2

(12) United States Plant Patent
Kanazawa

(10) Patent No.: US PP22,331 P2
(45) Date of Patent: Dec. 13, 2011

(54) **VARIETY OF *ANEMONE* PLANT NAMED 'PRETTY LADY SUSAN'**

(50) Latin Name: *Anemone hupehensis*
Varietal Denomination: Pretty Lady Susan

(75) Inventor: Yoshihiro Kanazawa, Yamatsuri (JP)

(73) Assignee: Walter Blom Plants B.V., Hillegom (NL)

( * ) Notice: Subject to any disclaimer, the term of this patent is extended or adjusted under 35 U.S.C. 154(b) by 0 days.

(21) Appl. No.: 12/800,749

(22) Filed: May 21, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — The Webb Law Firm

(57) ABSTRACT

A new and distinct *Anemone* plant named 'Pretty Lady Susan' having a compact growth habit and large deep pink-colored flowers.

3 Drawing Sheets

Botanical classification: *Anemone hupehensis.*
Varietal denomination: 'Pretty Lady Susan'.

BACKGROUND OF THE INVENTION

The present invention comprises a new and distinct cultivar of *Anemone* plant known by the varietal name 'Pretty Lady Susan'. The new variety was discovered in August of 2005 in a selected breeding program in Fukushima, Japan. The purpose of the breeding program was to produce a selection of *Anemone* varieties in a range of flower colors with compact growth habits that are freely flowering. The new variety was selected from a cross of *Anemone hupehensis* varieties 'Japonica' (female parent, unpatented) and 'Diana' (male parent, unpatented). The single flowers of the new variety are similar to its parents, but the new variety differs from its parents in increased flower size, improved flower color, a compact growth habit, and increased flower production. Further, 'Pretty Lady Susan' has a similar flower color to *Anemone hupehensis* variety 'Japonica Splendens' (unpatented), but differs in flower height and the number of flowers produced. Additionally, 'Pretty Lady Susan' has deep pink flowers of uniform color, whereas *Anemone hupehensis* variety 'Pretty Lady Diana' (U.S. Plant patent application Ser. No. 12/800,741) has bi-colored flowers with deep rose pink and light pink. The new variety was first asexually reproduced in October of 2005 by root cuttings in Fukushima, Japan. The new variety has been trial and field tested and has been found to retain its distinctive characteristics and remain true to type through successive propagations.

The following traits also distinguish 'Pretty Lady Susan' as a new and distinct cultivar from other *Anemone* varieties known to the breeder:

1. Compact growth habit;
2. Flower height;
3. Quantity of flowers produced;
4. Flower size; and
5. Flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
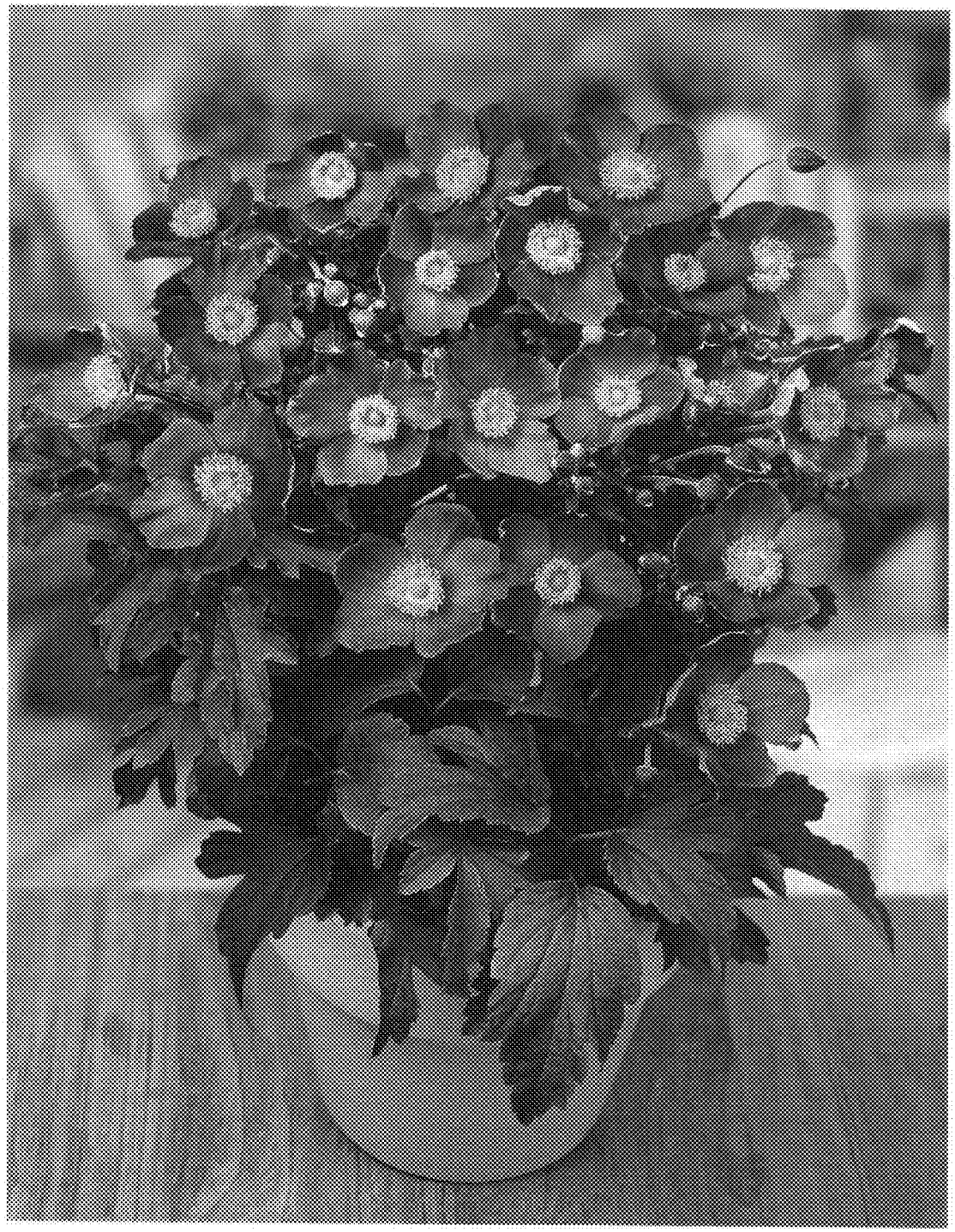
FIG. 1 is a photograph of the plant.
Figure 2:
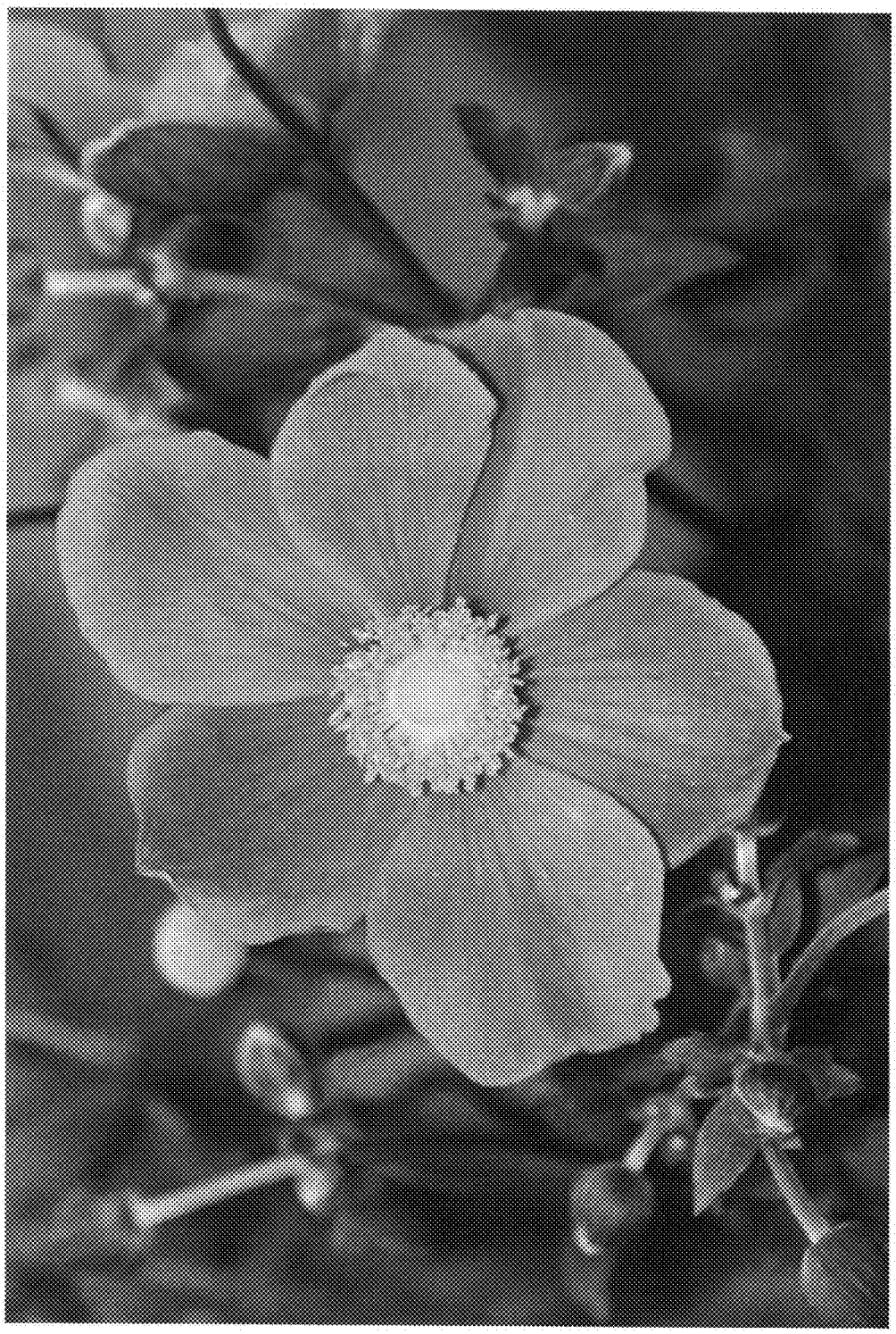
FIGS. 2 and 3 are close-up photographs of the flowers of the new variety.
Figure 3:
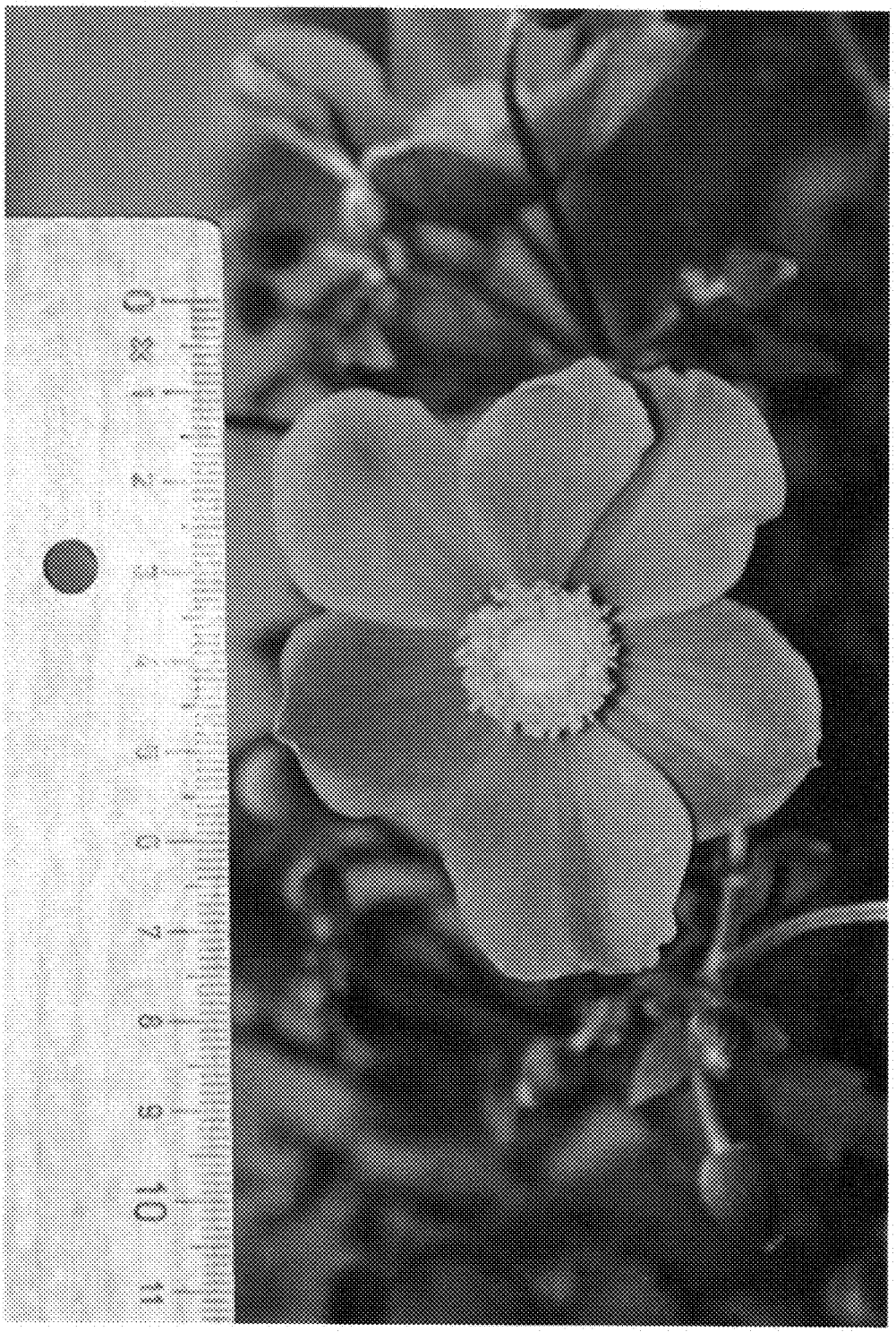

The following detailed description sets forth characteristics of the new cultivar. The data which defines these characteristics was collected after the new variety was grown from plugs propagated via tissue culture at 18 weeks. The plugs were planted directly in 21 cm diameter pots in Hillegom, The Netherlands outside in week 20, 2009. The data was collected in week 38, 2009 under natural daylight. Color references are primarily to The 2001 R.H.S. Colour Chart of The Royal Horticultural Society of London.

PLANT

Height: Approximately 50 cm.
Diameter: Approximately 40 cm.
Vigor: Good; plants produce up to 20 flower stems.
Roots:
- *Time to initiate roots.*—About 7 days at 20° C.
- *Time to develop roots.*—About 14 days at 20° C.

Time to finish a flowered plant: About 16 weeks in a 21 cm container.
Rooting habit and description: Roots are light brown and freely branching with fine root hairs present.
Branching habit: Caudex, basal foliage with a separate flower stem arising from the base.
Basal shoot:
- *Length.*—Average of 45 cm.
- *Diameter.*—Average of 2.5 mm.
- *Color.*—144A.
- *Texture.*—Smooth.
- *Internodes.*—None present; at 28 cm the new variety produces a group of leaves and then flowers.

Foliage:
- *Arrangement.*—Single, trifoliate.
- *Size of leaf.*—Length: Average of 7.5 cm. Width: Average of 4.2 cm.

*Shape of leaf.*—Basal foliage has a single petiole with trifoliate foliage.
*Shape of apex.*—Acute.
*Shape of base.*—Acute.
*Aspect.*—Horizontal to slightly above horizontal.
*Margin.*—Toothed; serrate to occasionally doubly serrate.
*Texture.*—Smooth.
*Color.*—Young leaves: Upper surface: 146A. Lower surface: 147B. Mature leaves: Upper surface: 137A. Lower surface: 147B.
*Petiole.*—Length: Center leaflet: Average of 2 cm. Side leaflets: Average of 0.5 cm. Diameter: Average of 2.0 mm. Texture: Smooth. Color: 144B.
*Veins.*—Venation type: Reticulate. Color: Upper surface: 147B. Lower surface: 147B.

FLOWER

Bud:
*Stage of opening when described.*—Tight.
*Shape.*—Globular and slightly pointed.
*Diameter.*—Average of 10 mm.
*Length.*—Average of 12 mm.
*Color.*—145B and shaded 184B.
Natural flowering season: Overwintered plants will flower from early July until late August or early September, spring planted plants will flower from mid-August until mid-September or early October.
Flower type and habit: Single flowers with 1 to 4 flowers per flowering stem.
Number of flowers per inflorescence: From 1 to 4 flowers per flowering stem.
Inflorescence height: Average of 15 cm.
Inflorescence diameter: Average of 11 cm.
Fragrance: None present.
Calyx:
*Diameter.*—Average of 6 cm.
*Depth.*—Average of 1 cm.
*Sepals.*—Number per calyx: 5. Length: 28 mm. Width: 17 mm. Aspect: Lying flat or slightly curved inward. Apex: Broadly rounded. Base: Cuneate. Margin: Smooth; entire. Texture and appearance: Smooth and satiny. Color: When opening: Upper surface: 74B. Lower surface: 74C. Fully opened: Upper surface: 74C. Lower surface: 77C.
Peduncles:
*Length.*—Between 3 cm and 11 cm.
*Diameter.*—Average of 2 mm.
*Aspect.*—Vertical.
*Texture.*—Smooth.
*Color.*—144B.
Pedicels:
*Length.*—Average of 25 cm.
*Diameter.*—Average of 2.5 mm.
*Aspect.*—Vertical.
*Texture.*—Smooth.
*Color.*—144A.
Disease resistance: Good.
Temperature tolerance: Good, up to +35° C.
Typical and observed lasting quality: Medium to good; 7 days.

REPRODUCTIVE ORGANS

Stamens:
*Number per flower.*—More than 240.
*Filament.*—Length: Approximately 7 mm. Diameter: Less than 1 mm.
*Anthers.*—Shape: Ellipsoid. Length: Approximately 1.5 mm. Color: 17C.
*Pollen.*—Color: 17C. Amount: Plentiful.
Pistils:
*Number per flower.*—More than 180.
*Length.*—Approximately 1.9 mm.
*Style.*—Length: Approximately 1.5 mm. Color: 157B.
*Stigma color.*—144B.
Seed/fruit production: None observed to date.

I claim:

1. A new and distinct variety of *Anemone* plant named 'Pretty Lady Susan' as shown and described herein.

* * * * *